US011419996B2

(12) United States Patent
Geske et al.

(10) Patent No.: US 11,419,996 B2
(45) Date of Patent: Aug. 23, 2022

(54) DEVICE FOR RESPIRATION BY USING A TUBUS

(71) Applicant: Loewenstein Medical Technology S.A., Luxembourg (LU)

(72) Inventors: Ralf Geske, Brunn (DE); Peter Kremeier, Karlsruhe (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 828 days.

(21) Appl. No.: 16/180,189

(22) Filed: Nov. 5, 2018

(65) Prior Publication Data

US 2019/0151582 A1 May 23, 2019

(30) Foreign Application Priority Data

Nov. 7, 2017 (DE) .......................... 102017010269.4

(51) Int. Cl.
*A61M 16/00* (2006.01)
*A61M 16/04* (2006.01)
(Continued)

(52) U.S. Cl.
CPC ...... *A61M 16/0009* (2014.02); *A61M 16/024* (2017.08); *A61M 16/04* (2013.01);
(Continued)

(58) Field of Classification Search
CPC .............. A61M 16/00; A61M 16/0003; A61M 16/0006; A61M 16/0009; A61M 16/0012; A61M 16/021; A61M 16/022; A61M 16/024; A61M 16/026; A61M 16/04; A61M 16/105; A61M 16/06; A61M 16/20; A61M 16/201; A61M 16/202; A61M 16/203; A61M 16/204; A61M 16/205; A61M 2016/0015; A61M 2016/0018;
(Continued)

(56) References Cited

U.S. PATENT DOCUMENTS 5,632,269 A * 5/1997 Zdrojkowski ....... A61M 16/026
128/204.21
5,694,923 A * 12/1997 Hete ..................... A61M 16/20
128/204.18
(Continued)

FOREIGN PATENT DOCUMENTS

DE 4116608 A1 11/1991
DE 4038871 A1 6/1992
(Continued)

*Primary Examiner* — Joseph D. Boecker
*Assistant Examiner* — Brian T Khong
(74) *Attorney, Agent, or Firm* — Abel Schillinger, LLP (57) ABSTRACT

The invention relates to a breathing apparatus, which comprises a respiratory gas source, a control unit and a device for connection to a tube. The control unit of the apparatus is connected to at least one sensor for recording a measurement value, the control unit comprising a pressure generator for setting at least two pressure levels generated by the respiratory gas source and a memory for measurement values, and the sensor being configured for measuring a flow and being coupled to an analyzer which determines the volume. The apparatus operates as specified in the claims.

20 Claims, 5 Drawing Sheets

(51) Int. Cl.
*A61M 16/10* (2006.01)
*A61M 16/06* (2006.01)
*A61M 16/20* (2006.01)

(52) U.S. Cl.
CPC ....... *A61M 16/105* (2013.01); *A61M 16/0006* (2014.02); *A61M 16/06* (2013.01); *A61M 16/20* (2013.01); *A61M 2016/003* (2013.01); *A61M 2016/0027* (2013.01)

(58) Field of Classification Search
CPC .. A61M 2016/0021; A61M 2016/0024; A61M 2016/0027; A61M 2016/003; A61M 2016/0033; A61M 2016/0036; A61M 2016/0039; A61M 2016/0042; A61M 2205/3327; A61M 2205/3331; A61M 2230/46; A61M 16/0057; A61M 16/0066; A61M 16/0069; A61M 2205/3334; A61M 2205/52; A61B 5/7275
See application file for complete search history.

(56) References Cited

U.S. PATENT DOCUMENTS

| | | | | |
|---|---|---|---|---|
| 5,921,238 | A * | 7/1999 | Bourdon | A61M 16/022 128/204.23 |
| 6,467,477 | B1 * | 10/2002 | Frank | A61M 16/024 128/203.23 |
| 6,920,875 | B1 | 7/2005 | Hill | |
| 7,886,739 | B2 * | 2/2011 | Soliman | A61M 16/0051 128/204.21 |
| 2001/0035186 | A1 * | 11/2001 | Hill | A61M 16/00 128/204.18 |
| 2003/0000526 | A1 * | 1/2003 | Gobel | A61M 16/0409 128/204.18 |
| 2003/0066528 | A1 * | 4/2003 | Hill | A61M 16/026 128/204.18 |
| 2003/0121519 | A1 * | 7/2003 | Estes | A61M 16/0069 128/204.18 |
| 2004/0016433 | A1 * | 1/2004 | Estes | A61M 16/0051 128/204.21 |
| 2006/0086357 | A1 * | 4/2006 | Soliman | A61M 16/0833 128/204.22 |
| 2007/0101992 | A1 * | 5/2007 | Soliman | A61M 16/026 128/204.21 |
| 2007/0272241 | A1 * | 11/2007 | Sanborn | A61M 16/0051 128/204.23 |
| 2008/0091117 | A1 | 4/2008 | Choncholas | |
| 2009/0050154 | A1 * | 2/2009 | Strothmann | A61M 16/0069 128/204.23 |
| 2010/0288283 | A1 | 11/2010 | Campbell | |
| 2010/0319691 | A1 * | 12/2010 | Lurie | A61M 16/201 128/203.12 |
| 2012/0216809 | A1 * | 8/2012 | Milne | A61B 5/087 128/204.18 |
| 2013/0220324 | A1 * | 8/2013 | Jafari | A61M 16/0006 128/204.23 |
| 2016/0067434 | A1 * | 3/2016 | Schwaibold | A61M 16/0051 128/202.22 |

FOREIGN PATENT DOCUMENTS

| | | |
|---|---|---|
| DE | 19528113 A1 | 2/1997 |
| DE | 102007047105 A1 | 4/2008 |
| EP | 2644220 A1 | 10/2013 |
| EP | 3061481 A1 | 8/2016 |

\* cited by examiner

DEVICE FOR RESPIRATION BY USING A TUBUS

CROSS-REFERENCE TO RELATED APPLICATIONS

The present application claims priority under 35 U.S.C. § 119 of German Patent Application No. 102017010269.4, filed on Nov. 7, 2017, the entire disclosure of which is expressly incorporated by reference herein.

BACKGROUND OF THE INVENTION

1. Field of the Invention

The invention relates to an apparatus for breathing while taking into account the influences of an endotracheal tube (ETT), or an endotracheal cannula.

2. Discussion of Background Information

An endotracheal tube (ETT), or an endotracheal cannula, is a flexible plastic tube which is placed in the trachea for breathing. Because of their small internal diameter, the ETT, or the tracheal cannula, influence the overall resistance of the respiratory system during breathing. If a narrower tube is used, then there will be a greater pressure difference for the same gas flow. Tube models of different manufacturers furthermore differ in their tube-specific resistance.

Various methods have been proposed in order to compensate for the increased resistance of the ETT.

The tube compensation (ATC) of the company Dräger offers an automatic increase of the pressure as a function of characteristic data of the ETT (tube length and/or tube diameter). To this end, however, the values of the tube must be input at the start. Furthermore, a constant measurement of the gas flow and subsequent readjustment of the pressure are necessary, which may lead to control oscillations and therefore make the breathing inefficient.

In this case, the fact is not taken into account that deposits, which may significantly change the resistance of the ETT, may form in the ETT during breathing. A length reduction of the ETT, which the doctor often carries out at the start of the breathing, furthermore reduces the tube-specific resistance.

DE 4116608 A1, the entire disclosure of which is incorporated by reference herein, proposes to determine the pressure in the lungs for tube compensation. To this end, a pressure sensor is inserted through the tube into the trachea. The pressure sensor additionally increases the tube-specific resistance. Furthermore, the pressure sensor may easily be obstructed by mucus.

There is therefore a need for a simple apparatus for tube compensation, which functions without prior knowledge of the tube-specific resistances and without prior input of tube characteristic data.

It would therefore be advantageous to have available a simple and robust apparatus for tube compensation. In this case, improved breathing is intended to be achieved while taking into account the influences of an endotracheal tube (ETT) or of an endotracheal cannula (both referred to as a tube for simplicity).

SUMMARY OF THE INVENTION

The present invention provides a breathing apparatus, which comprises a respiratory gas source, a control unit and a device for connection to a tube. The control unit of the apparatus is connected to at least one sensor for recording a measurement value, the control unit comprising a pressure generator for setting at least two pressure levels generated by the respiratory gas source, the control unit comprising a memory for measurement values, the sensor being configured for measuring a flow, and being coupled to an analyzer which determines the volume, and the pressure generator setting the pressure initially to an expiratory level Pe1 and then to an inspiratory level Pi1, the sensor determining the flow and the analyzer determining the resulting volume of V1 and storing it in the memory, the pressure generator in a subsequent cycle increasing the pressure from the expiratory level Pe1 with a predeterminable pressure profile to an inspiratory level Pi2, the sensor determining the flow and the analyzer determining the volume V2, the pressure generator reducing the pressure to a lower pressure level whenever the volume V2 has reached a predefined fraction of the volume V1.

As an alternative or in addition, provision is also made that the pressure generator reduces the pressure to a lower pressure level only when the volume V2 has reached a predefined fraction of the volume V1 and/or the flow has decreased to a predetermined level and/or the predefined fraction of the volume V1 has flowed in a predefined time (for example 50-500 ms).

The apparatus is, for example, additionally one wherein the pressure Pi2 is higher than the pressure Pi1 and corresponds to a predetermined maximum pressure Pmax.

The apparatus is, for example, additionally one wherein the pressure Pi2 corresponds to a predetermined Pmax—1 to 6 mbar, for example Pmax—3 mbar.

The apparatus is, for example, additionally one wherein the predeterminable pressure profile corresponds to a pressure ramp of 50-380 ms.

The apparatus is, for example, additionally one wherein the predeterminable pressure profile corresponds to a pressure ramp of 100-300 ms.

The apparatus is, for example, additionally one wherein the predeterminable pressure profile corresponds to a sine function.

The apparatus is, for example, additionally one wherein the predeterminable pressure profile corresponds to an exponential function or an arbitrary rising function.

The apparatus is, for example, additionally one wherein the pressure generator, starting from the pressure Pe1, sets the pressure Pi2 and in this case the volume V2 is reached in a time of 100-600 ms, or of 300-400 ms.

The apparatus is, for example, additionally one wherein the predetermined level of the flow is 5-20 l/min.

The apparatus is, for example, additionally one wherein the predeterminable pressure profile corresponds to the pressure profile adjusted at the ventilator.

The apparatus is, for example, additionally one wherein, when a time of 200-400 ms, preferably 300 ms, is fallen below, the pressure Pi2 is reduced for the next breathing cycle.

The apparatus is, for example, additionally also one wherein, when a time of 250-450 ms, preferably 350 ms, is exceeded, the pressure Pi2 is increased for the next breathing cycle.

The apparatus is, for example, additionally also one wherein the volume V2 is 60-95%, or 70-90%, of the volume V1.

The apparatus is, for example, additionally one wherein, after the low expiratory pressure level Pe1 has been set, a higher expiratory pressure level Pe2 is set.

The apparatus is, for example, additionally also one wherein, after the expiratory pressure level Pe2 has been set, the low pressure level Pe1 is set again and then the inspiratory pressure level Pi1 or Pi2 is set.

The apparatus is, for example, additionally also one wherein, after the expiratory pressure level Pe2 has been set, the pressure level Pi1 or Pi2 is set.

The apparatus is, for example, additionally one wherein at least one increasing pressure profile and/or at least one decreasing pressure profile are settable.

The apparatus is, for example, additionally also one wherein at least one pressure profile is controlled as a function of a flow or of a volume.

The apparatus is, for example, additionally one wherein the pressure generator, starting from the pressure Pi2, sets the pressure Pi1 when the volume V2 has reached a predefined fraction of the volume.

The apparatus is, for example, additionally also one wherein the pressure generator, starting from the pressure Pi2, also sets the pressure Pe1 when the volume V2 has reached a predefined fraction of the volume.

BRIEF DESCRIPTION OF THE DRAWINGS

Other features and advantages of the present invention may be found in the description of embodiments of the invention, which will be explained below with reference to the appended figures.

In the figures.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
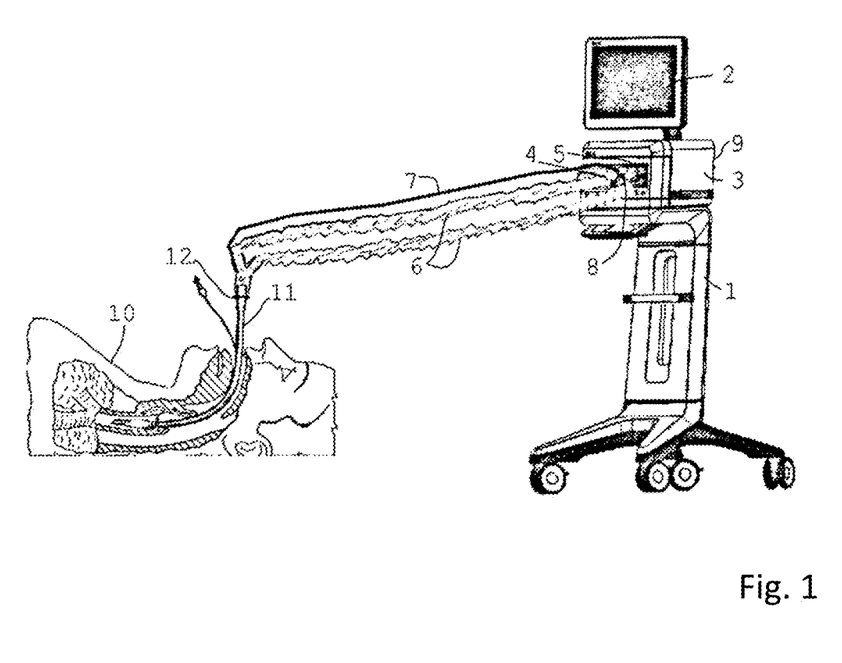
FIG. 1 shows the basic structure of a breathing apparatus.

FIG. 1 shows the basic structure of a breathing apparatus. In the region of an equipment housing (1) having a control panel and a display (2), a respiratory gas source (3) is arranged in an equipment interior. The respiratory gas source may be a fan or a compressed gas source. A hose system (6) is connected by means of the couplings (4, 5). An additional pressure measuring hose (7), which can be connected by means of a pressure input connector (8) to the equipment housing (1), may extend along the hose system (6). In order to permit data transmission, the equipment housing (1) comprises an interface (9) (not shown in the figure).

FIG. 1 furthermore shows an intubated patient (10) having an endotracheal tube (11) and a connector (12) for the breathing hose system (6).

Figure 2A:
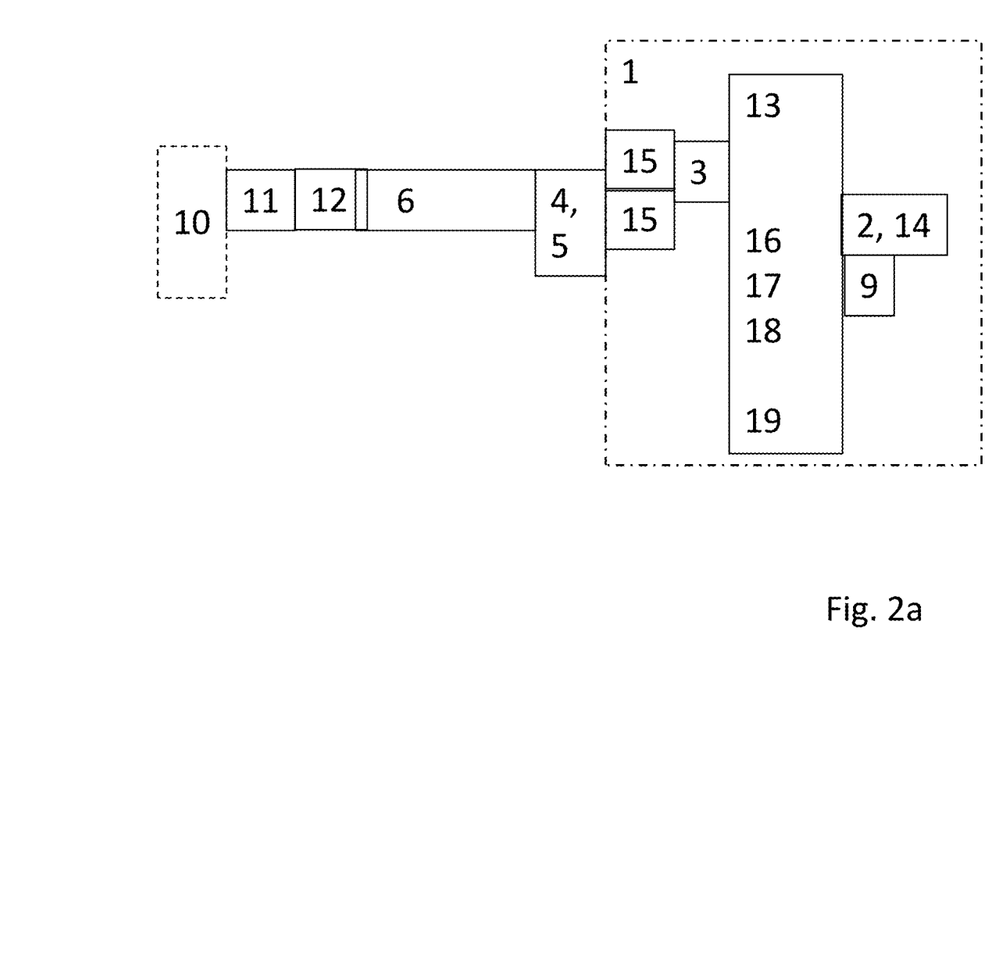
FIGS. 2a and 2b show the outline structure of a control-technology apparatus component.
Figure 2B:
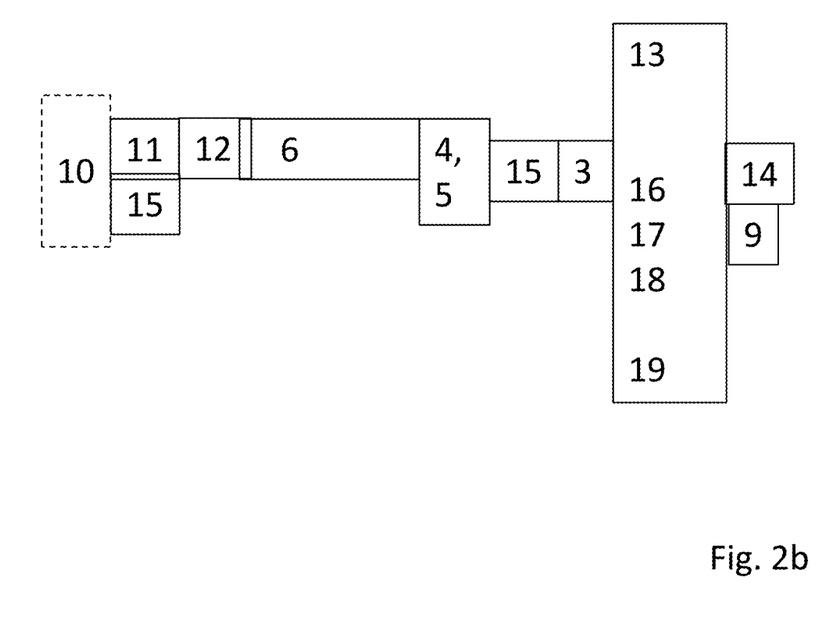

FIG. 2a and FIG. 2b show the outline structure of the control-technology apparatus components. A control unit (13) is provided with an input module (14) (not represented) for data input. The input module may be a touchscreen (2). By means of the input module (14) setpoint values for the breathing may be input, for example by a doctor. The control unit (13) is connected to a sensor (15), which records at least one breathing parameter of a patient. In the exemplary embodiment represented, the sensor (15) is configured as a flow sensor, the measurement signal of which is delivered to an integrator (17) in order to determine a volume value. In addition, a pressure sensor may be provided. The sensor or sensors may be provided in the region of the apparatus (1) and/or in the vicinity of the patient (10) or tube (11). The integrator (17) is connected to an analyzer (18) for evaluating the volume profile. The analyzer (18) may also jointly undertake the function of the integrator (17). The analyzer is also supplied with the comparative value for the volume, stored in the region of the memory (16). Furthermore, the analyzer (18) is connected to a pressure generator (19) which sets a respective setpoint pressure for the respiratory gas source (3).

Figure 3A:
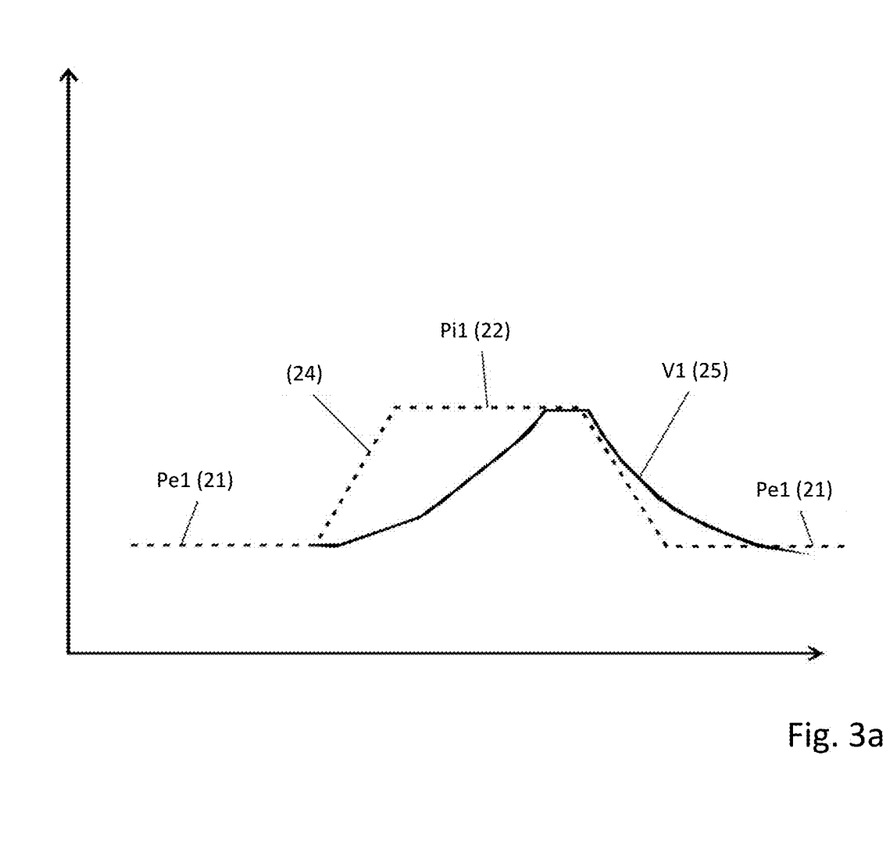
FIG. 3a shows the profile of pressure and volume when using the tube compensation according to the invention without compensation.
Figure 3B:
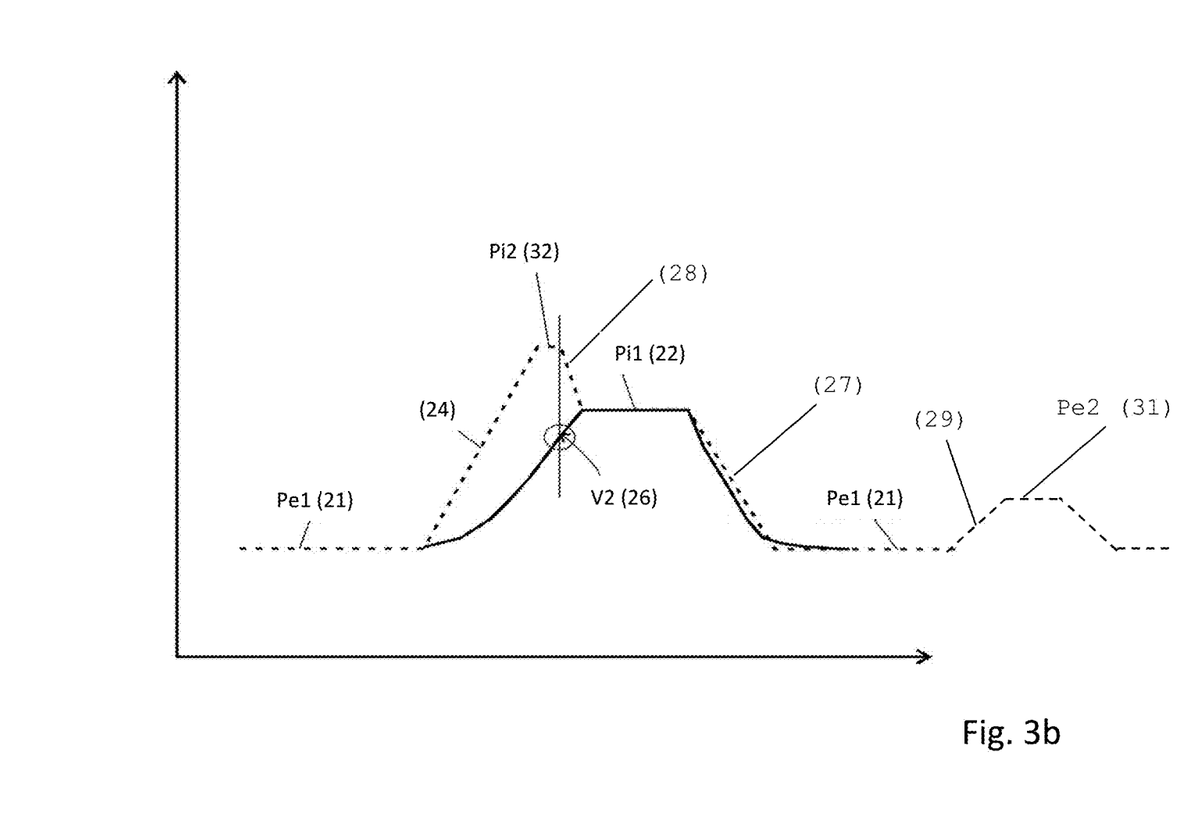
FIG. 3b shows the profile of pressure and volume when using the tube compensation according to the invention with compensation.

FIG. 3 shows the profile of pressure and volume when using the tube compensation according to the invention. The tube compensation according to the invention may, for example, be carried out in the scope of a bilevel mode, or also in the case of a patient-triggered bilevel mode. In this case, the pressure difference is predetermined and the volume is given by the pressure difference and the overall compliance. As an alternative, there is an enhanced form of the bilevel with volume guarantee. In this case, the volume is predetermined and the pressure difference is adapted.

a) At first, no compensation is carried out, but instead the pressure-based breathing, adjusted by the user, with volume control. After for example 2 to 5 breathing cycles, the applied tidal volume V1 (25) is known (volume control). This is used as a starting value. As an alternative, the compliance may also be used for calculations. In the case of pressure-regulated constant-volume breathing, the applied tidal volume is predetermined.

The pressure generator (19) sets the pressure initially to an expiratory level Pe1 (21) and then to an inspiratory level Pi1 (22). The volume is given passively by the predetermined pressure difference Pe1-Pi1, if no volume-based breathing has been adjusted. In the case of volume-based breathing, the volume is predetermined and the pressure difference is adapted.

Subsequently, the pressure generator (19) reduces the pressure to the expiratory level Pe1 (21). The sensor (15) determines the gas flow, and the analyzer (18) determines the volume V1 (25), which is stored in the memory (16).

b)

In a subsequent cycle, the pressure generator (19) sets the pressure to the expiratory level Pe1 (21) and then increases the pressure with a predetermined pressure profile (24) to an inspiratory level Pi2 (32). The sensor (15) determines the flow, and the analyzer (18) determines the volume V2 (26). The pressure generator (19) reduces the pressure to the level Pi1 (22) only when the volume V2 (26) has reached a predefined fraction, for example 80%, of the volume V1 (25). To this end, the control unit (13) compares the volume V1 (25) from the memory with the volume V2 (26) and/or the flow has fallen to a predefined value, for example 5-15 l/min, and/or the predetermined time has been exceeded, for example 300 ms.

According to the invention, no compensation (of the tube) takes place at first, but instead the pressure-based breathing (with volume control) adjusted by the user. After for example 2 to 5 breathing cycles, the applied tidal volume V1 (25) is known. This is used as a starting value. As an alternative, the compliance may also be used for calculations. In the case of pressure-regulated constant-volume breathing, the applied tidal volume is predetermined.

The pressure is then increased at the start of the next inspiration (controlled or triggered) temporarily to a level of Pmax—3 mbar (Pi2 (32). The pressure ramp (slope of the opening of the proportional valves) may in this case be 200 ms, for example, or correspond to a sine function or to any other desired function, for example an exponential function.

With this pressure (32), the applied tidal volume is measured. When this has reached 80% of the required tidal volume V1 (25), for example, the pressure is reduced to the adjusted plateau pressure Pi1 (22). The further inspiration then takes place at this pressure with reduced flow. In the case of pressure-regulation constant-volume breathing, the pressure regulation takes place in the usual way.

The application of 80% of V1 should take place in a predetermined time. In this case, a time of for example 100-600 ms, preferably 300 ms, is employed. If it is found that this time has been fallen below, the initial pressure Pmax—3 mbar is to be reduced in steps of 1 mbar until a stable situation has been established.

In the case of the adjusted pressure difference (bilevel) or the regulated pressure difference (bilevel with volume guarantee), the pressure Pi2 (32) at the start of the breathing cycle is increased to a predetermined level of Pmax, for example Pmax—3 mbar, with a ramp of for example 90-300 ms. The maximum pressure Pmax is in this case preadjusted or is predeterminable by the user.

In this case, and increased plateau pressure in comparison with Pi1 (22) is set up at which the volume is not yet fully applied. Only when, for example, 50%-80% of the volume V1 (25) is reached is the pressure reduced again to its initial value Pi1 (22) (adjusted pressure difference or adapted pressure difference). The resistance (flow resistance of the tube and inspiration hose) is intended to be compensated for by this maneuver. The ramp of for example 50-380 ms, preferably 100-300 ms, particularly preferably 150-250 ms, is in this case also selected in such a way that the volume does not enter the lungs too rapidly, in order to avoid damage due to shear stresses.

In the scope of the invention, the pressure gradient may also be not constant but instead correspond to a function, for example a sine function or an exponential function, or a function which allows adaptation to physiological conditions.

In expiration, the pressure in the hose system is reduced when necessary at most to ambient pressure. The control ensures that the pressure at the tube tip does not fall below the adjusted PEEP pressure (or CPAP pressure). In the case of obstructive patients, it may be expedient to keep the pressure at the tube tip above the adjusted CPAP pressure for a longer time. During the expiration flow phase, obstructive regions are therefore kept open for a longer time.

According to the invention, after the setting of the low expiratory pressure level Pe1 (21), a higher expiratory pressure level Pe2 (31) can be set.

According to the invention, provision may be made for the pressure profile (28) and/or the pressure profile (27) and/or the pressure profile (29) to be predeterminably controlled, for example as a function of the flow or the volume.

What is claimed is:

1. A breathing apparatus, wherein the apparatus comprises a respiratory gas source, a control unit and a device for connection to an endotracheal tube or endotracheal cannula, the control unit being connected to at least one sensor for recording at least one measurement value and comprising a pressure generator for setting at least two pressure levels generated by the respiratory gas source and a memory for the measurement values, the at least one sensor being configured for measuring a flow and being coupled to an analyzer which determines a volume, and the pressure generator setting a pressure initially to an expiratory level Pe1 and then to an inspiratory level Pi1, the at least one sensor determining the flow and the analyzer determining a resulting volume V1 and storing V1 in the memory, the pressure generator in a subsequent breathing cycle increasing the pressure from the expiratory level Pe1 with a predeterminable pressure profile to an inspiratory level Pi2, the pressure Pi2 being higher than the pressure Pi1, the at least one sensor determining the flow and the analyzer determining a volume V2, the pressure generator reducing the pressure to a pressure level which is lower than Pi2 only when the volume V2 has reached a predefined fraction of the volume V1.

2. The apparatus of claim 1, wherein the pressure Pi2 corresponds to a predetermined maximum pressure Pmax.

3. The apparatus of claim 2, wherein the predetermined Pmax is from 1 to 6 mbar.

4. The apparatus of claim 1, wherein the predeterminable pressure profile corresponds to a pressure ramp of 50-380 ms.

5. The apparatus of claim 1, wherein the predeterminable pressure profile corresponds to a pressure ramp predetermined by a user or the breathing apparatus.

6. The apparatus of claim 1, wherein the pressure generator, starting from the pressure Pe1, sets the pressure Pi2 and, in this case, the volume V2 is reached in a predetermined time.

7. The apparatus of claim 6, wherein the predetermined time is 100-600 ms.

8. The apparatus of claim 1, wherein the pressure generator, starting from the pressure Pe1, sets the pressure Pi2 and the flow reaches a predetermined level.

9. The apparatus of claim 8, wherein the predetermined level of the flow is 5-20 l/min.

10. The apparatus of claim 1, wherein the pressure generator, starting from the pressure Pe1, sets the pressure Pi2 and, in this case, the volume V2 is reached in a time of 300-400 ms.

11. The apparatus of claim 1, wherein, when a time it takes to reach V2 is shorter than 200-400 ms, the pressure Pi2 is reduced for the next breathing cycle, and when a time it takes to reach V2 is longer than 250-450 ms, the pressure Pi2 is increased for the next breathing cycle.

12. The apparatus of claim 1, wherein the volume V2 is 60-95% of the volume V1.

13. The apparatus of claim 1, wherein, after an expiratory pressure level Pe2 has been set, the low pressure level Pe1 is set again and then the inspiratory pressure level Pi1 or Pi2 is set.

14. The apparatus of claim 1, wherein the pressure profile is controlled as a function of flow.

15. The apparatus of claim 1, wherein the pressure generator, starting from the pressure Pi2, sets the pressure Pi1 when the volume V2 has reached the predefined fraction of the volume V1.

16. The apparatus of claim 1, wherein the pressure profile is controlled as a function of V1 and/or V2.

17. A breathing apparatus, wherein the apparatus comprises a respiratory gas source, a control unit and a device for connection to an endotracheal tube or endotracheal cannula, the control unit being connected to at least one sensor for recording a measurement value and comprising a pressure generator for setting at least two pressure levels generated by the respiratory gas source and a memory for the measurement values, the at least one sensor being configured for measuring a flow and being coupled to an analyzer which determines the volume, and the pressure generator setting a pressure initially to an expiratory level Pe1 and then to an inspiratory level Pi1, the at least one sensor determining the flow and the analyzer determining a resulting volume V1 and storing V1 in the memory, the pressure generator in a subsequent breathing cycle increasing the pressure from the expiratory level Pi1 with a pressure profile to an inspiratory level Pi2, the pressure Pi2 being higher than the pressure Pi1, the at least one sensor determining the flow and the analyzer determining a volume V2, the pressure generator reducing the pressure to a lower pressure level than Pi2 only when the volume V2 has reached a predefined fraction of the volume V1 and/or the flow has decreased to a predetermined level and/or the predefined fraction of the volume V1 has flowed in a predefined time.

18. The apparatus of claim 17, wherein the pressure generator reduces the pressure to a lower pressure than Pi2 only when the predefined faction of the volume V1 has flowed in a predefined time, the predefined time being 50-500 ms.

19. The apparatus of claim 17, wherein the pressure generator reduces the pressure to a lower pressure than Pi2 only when the flow has decreased to a predetermined level.

20. A breathing apparatus, wherein the apparatus comprises a respiratory gas source, a control unit and a device for connection to an endotracheal tube or endotracheal cannula, the control unit being connected to at least one sensor for recording at least one measurement value and comprising a pressure generator for setting at least two pressure levels generated by the respiratory gas source and a memory for the measurement values, the at least one sensor being configured for measuring a flow and being coupled to an analyzer which determines a volume, and the pressure generator setting a pressure initially to an expiratory level Pe1 and then to an inspiratory level Pi1, the at least one sensor determining the flow and the analyzer determining a resulting volume V1 and storing V1 in the memory, the pressure generator in a subsequent breathing cycle increasing the pressure from the expiratory level Pe1 with a predeterminable pressure profile to an inspiratory level Pi2, the at least one sensor determining the flow and the analyzer determining a volume V2, the pressure generator reducing the pressure to a pressure level which is lower than Pi2 only when the volume V2 has reached a predefined fraction of the volume V1 and wherein, when a time it takes to reach V2 is shorter than 200-400 ms, the pressure Pi2 is reduced for the next breathing cycle, and when a time it takes to reach V2 is longer than 250-450 ms, the pressure Pi2 is increased for the next breathing cycle.

* * * * *